US00PP36268P2

(12) United States Plant Patent
Mousa

(10) Patent No.: US PP36,268 P2
(45) Date of Patent: Nov. 26, 2024

(54) ***DAHLIA* PLANT NAMED 'Dodahyptrobre'**

(50) Latin Name: *Dahlia variabilis*
Varietal Denomination: Dodahyptrobre

(71) Applicant: DUMMEN GROUP B.V., De Lier (NL)

(72) Inventor: Rami Mousa, De Lier (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 18/581,358

(22) Filed: Feb. 19, 2024

(51) Int. Cl.
*A01H 5/02* (2018.01)
*A01H 6/14* (2018.01)

(52) U.S. Cl.
USPC ..... Plt./321

(58) Field of Classification Search
USPC ..... Plt./263.1, 321
See application file for complete search history.

(56) References Cited

PUBLICATIONS

Roger's Gardens. 2024. https://plants.rogersgardens.com/12290002/Plant/24879/Dahlinova_Hypnotica_Tropical_Breeze_Dahlia/. retrived from the internet on Jun. 11, 2024. 3 pages. (Year: 2024).*

* cited by examiner

*Primary Examiner* — Karen M Redden
(74) *Attorney, Agent, or Firm* — C. Anne Whealy

(57) ABSTRACT

A new and distinct cultivar of *Dahlia* plant named 'Dodahyptrobre', characterized by its mostly upright and uniformly mounding plant habit; moderately vigorous growth habit and moderate growth rate; freely branching habit; dark green-colored leaves; freely flowering habit; large double-type inflorescences with reddish purple and yellow bicolored ray florets; good postproduction longevity; and good garden performance.

1 Drawing Sheet

Botanical designation: *Dahlia variabilis*.
Cultivar denomination: 'DODAHYPTROBRE'.

STATEMENT REGARDING PRIOR DISCLOSURES BY INVENTOR AND APPLICANT/ASSIGNEE

An European Community Plant Breeder's Rights application for the instant plant was filed by the Applicant/Assignee, Dümmen Group B.V. of De Lier, The Netherlands on Nov. 15, 2023, application number 2023/2276. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Dahlia* plant, botanically known as *Dahlia variabilis* and hereinafter referred to by the name 'Dodahyptrobre'.

The new *Dahlia* plant is a product of a planned breeding program conducted by the Inventor in De Lier, The Netherlands. The objective of the breeding program is to create new container *Dahlia* plants that have a freely branching and flowering habit, strong leaves, large attractive inflorescences and good postproduction longevity and garden performance.

The new *Dahlia* plant originated from a cross-pollination during the autumn of 2018 in De Lier, The Netherlands of a proprietary selection of *Dahlia variabilis* identified as code number DA-0727, not patented, as the female, or seed, parent with a proprietary selection of *Dahlia variabilis* identified as code number DA-0179, not patented, as the male, or pollen, patent. The new *Dahlia* plant was discovered and selected by the Inventors as a single flowering plant from within the progeny of the stated cross-pollination in a controlled greenhouse environment in De Lier, The Netherlands during the summer of 2019.

Asexual reproduction of the new *Dahlia* plant by vegetative terminal cuttings in a controlled greenhouse environment in De Lier, The Netherlands since the autumn of 2019 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodahyptrobre'. These characteristics in combination distinguish 'Dodahyptrobre' as a new and distinct *Dahlia* plant:

1. Mostly upright and uniformly mounding plant habit.

2. Moderately vigorous growth habit and moderate growth rate.
3. Freely branching habit.
4. Dark green-colored leaves.
5. Freely flowering habit.
6. Large double-type inflorescences with reddish purple and yellow bi-colored ray florets.
7. Good postproduction longevity.
8. Good garden performance.

Compared to plants of the female parent selection, plants of the new *Dahlia* differ primarily in ray floret color as ray florets of plants of the new *Dahlia* are reddish purple and yellow bi-colored whereas ray florets of plants of the female parent selection are white in color. In addition, plants of the new *Dahlia* have larger inflorescences than plants of the female parent selection.

Compared to plants of the male parent selection, plants of the new *Dahlia* differ primarily in garden performance as plants of the new *Dahlia* have good garden performance whereas plants of the male parent selection have poor garden performance. In addition, ray florets of plants of the new *Dahlia* resist fading under high light and high temperature conditions whereas ray florets of plants of the male parent selection fade under high light and high temperature conditions.

Plants of the new *Dahlia* can be compared to plants of *Dahlia variabilis* 'Dodahhypelpin', disclosed in U.S. Plant Pat. No. 31,639. In side-by-side comparisons, plants of the new *Dahlia* differ primarily from plants of 'Dodahhypelpin' in the following characteristics:

1. Plants of the new *Dahlia* are larger and stronger than plants of 'Dodahhypelpin'.
2. Plants of the new *Dahlia* are more freely flowering than plants of 'Dodahhypelpin'.
3. Ray florets of plants of the new *Dahlia* are reddish purple and yellow bi-colored whereas ray florets of plants of 'Dodahhypelpin' are reddish purple in color.
4. Plants of the new *Dahlia* have stronger garden performance than plants of 'Dodahhypelpin'.
5. Ray florets of plants of the new *Dahlia* resist fading under high light and high temperature conditions whereas ray florets of plants of 'Dodahhypelpin' fade under high light and high temperature conditions.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photograph may differ slightly from the color values cited in the detailed botanical description which accurately describe the colors of the new *Dahlia* plant.

The photograph is a side perspective view of a typical flowering plant of 'Dodahyptrobre' grown in a container.

DETAILED BOTANICAL DESCRIPTION

The aforementioned photograph and the following observations and measurements describe plants grown during the summer in 15-cm containers in a glass-covered greenhouse in De Lier, The Netherlands and under environmental conditions and cultural practices which approximate those generally used in commercial potted *Dahlia* production. During the production of the plants, day temperatures ranged from 18° C. to 30° C., night temperatures ranged from 16° C. to 22° C. and light levels were at least 135 watt/$m^2$. Plants were pinched one time about four weeks after sticking unrooted cuttings. Plants were twelve weeks old when the photograph was taken and eleven weeks old when the description was taken. In the following description, color references are made to The Royal Horticultural Society Colour Chart, Fifth Edition, except where general terms of ordinary dictionary significance are used.

Botanical classification: *Dahlia variabilis* 'Dodahyptrobre'.

Parentage:

*Female, or seed, parent*.—Proprietary selection of *Dahlia variabilis*identified as code number DA-0727, not patented.

*Male, or pollen, parent*.—Proprietary selection of *Dahlia variabilis*identified as code number DA-0179, not patented.

Propagation:

*Type*.—By vegetative terminal cuttings.

*Time to initiate roots, summer*.—About twelve days at temperatures about 22° C. to 30° C.

*Time to initiate roots, winter*.—About 14 days at temperatures about 20° C. to 22° C.

*Time to produce a rooted plant, summer*.—About 21 days at temperatures about 22° C. to 30° C.

*Time to produce a rooted plant, winter*.—About 24 days at temperatures about 20° C. to 22° C.

*Root description*.—Medium in thickness, fibrous; typically whitish grey in color, actual color of the roots is dependent on substrate composition, water quality, fertilizers, substrate temperature and age of roots; tuber development has not been observed on plants of the new *Dahlia*.

*Rooting habit*.—Moderately freely branching; medium density.

Plant description:

*Plant and growth habit*.—Mostly upright and uniformly mounding plant form; overall shape, globose; freely basal branching habit with about four primary lateral branches per plant each primarily lateral branch with about five secondary lateral branches; pinching enhances lateral branch development; inflorescences held above the foliar plane on moderately strong peduncles; bushy and dense habit; moderately vigorous growth habit and moderate growth rate.

*Plant height, soil level to top of foliar plane*.—About 22 cm.

*Plant height, soil level to top of floral plane*.—About 30 cm.

*Plant diameter or spread*.—About 30 cm.

*Lateral branches*.—Length: About 20 cm. Diameter: About 9 mm. Internode length: About 2 cm to 4 cm. Aspect: Mostly upright. Strength: Moderately strong. Texture and luster: Smooth, glabrous; semi-glossy. Color, developing: Close to 143C. Color, developed: Close to 143A.

Leaf description:

*Arrangement*.—Opposite; leaves may be single or compound with typically three leaflets.

*Leaf length*.—About 16 cm.

*Leaf width*.—About 15 cm.

*Leaflet length*.—About 10 cm.

*Leaflet width*.—About 6 cm.

*Leaf and leaflet shape*.—Ovate.

*Leaf and leaflet apex*.—Acute.

*Leaf and leaflet base*.—Attenuate.

*Leaf and leaflet margin*.—Dentate to crenate; occasionally lobed with indentations medium to deep in depth and divergent.

*Leaf and leaflet venation pattern*.—Pinnate.

*Leaf and leaflet texture and luster, upper surface*.—Smooth, glabrous; semi-glossy.

*Leaf and leaflet texture and luster, lower surface*.—Smooth, glabrous; matte.

*Color*.—Developing leaves and leaflets, upper surface: Close to 136A. Developing leaves and leaflets, lower surface: Close to 137C. Fully expanded leaves and leaflets, upper surface: Close to 136A; venation, close to 144A. Fully expanded leaves and leaflets, lower surface: Close to 138B; venation, close to 143A.

*Petioles*.—Length: About 4.5 cm. Diameter: About 4 mm. Strength: Moderately strong. Texture and luster, upper and lower surfaces: Smooth, glabrous; semi-glossy. Color, upper and lower surfaces: Close to 144A.

Inflorescence description:

*Appearance and arrangement*.—Double inflorescence form with ray florets forming acropetally on a receptacle; inflorescences positioned above the foliar plane on moderately strong peduncles; inflorescences face mostly upright; freely flowering habit with about twelve inflorescences per plant at one time.

*Fragrance*.—None detected.

*Time to flower*.—Early flowering habit, plants begin flowering about ten to twelve weeks after planting; in the garden in The Netherlands, plants flower continuously from spring until late summer.

*Post-production longevity*.—Inflorescences maintain good substance for about two to three weeks on the plant; inflorescences persistent.

*Inflorescence buds*.—Height: About 1 cm. Diameter: About 1 cm. Shape: Globular. Texture and luster: Smooth, glabrous; glossy. Color: Close to 144B.

*Inflorescence size*.—Diameter: Large, about 10.5 cm. Depth (height): About 2 cm to 3.5 cm. Disc diameter: About 2 cm; inconspicuous. Receptacle height: About 2 mm to 3 mm. Receptacle diameter: About 1.5 cm. Receptacle color: Close to 144A.

*Ray florets*.—Quantity per inflorescence: About 100 to 120 arranged in about eleven whorls. Length: About 5 cm. Width: About 1.5 cm. Shape: Oblong. Apex: Retuse. Base: Attenuate. Margin: Entire; not undulate. Aspect: Initially upright to roughly perpendicular to the peduncle; somewhat concave. Texture and luster, upper and lower surfaces: Smooth, glabrous; matte. Color: When opening, upper surface: Proximally, close to 7B and distally, close to 74B. When opening, lower surface: Close to 72D. Fully opened, upper surface: Proximally, close to 7B and distally, close to 74B; venation, close to 12A and 46A; colors becoming closer to 13C and 74C with subsequent development. Fully opened, lower surface: Close to 65B; venation, close to 4C; color becoming closer to 2C and 77B with subsequent development.

*Disc florets*.—Quantity per inflorescence: About 40 to 60; disc florets are inconspicuous. Length: About 8 mm. Diameter: About 1 mm. Shape: Tubular, elongated; apices retuse. Texture and luster: Smooth, glabrous; glossy. Color, fully opened, inner and outer surfaces: Close to 17B.

*Phyllaries*.—Quantity per inflorescence: About seven arranged in a single whorl. Length: About 1.5 cm. Width: About 5 mm to 8 mm. Shape: Ovate. Apex: Acute. Base: Attenuate. Margin: Entire. Texture and luster, upper and lower surfaces: Smooth, glabrous; semi-glossy. Color, upper surface: Close to 137A. Color, lower surface: Close to 137B.

*Peduncles*.—Length, terminal peduncle: About 5.5 cm to 6 cm. Diameter, terminal peduncle: About 3 mm. Aspect: Mostly erect to slightly outwardly. Strength: Moderately strong. Texture and luster: Smooth, glabrous; semi-glossy. Color: Close to 138B.

*Reproductive organs*.—Androecium: Present on disc florets only. Stamen quantity per floret: Five. Filament length: About 8 mm. Filament color: Close to 12B. Anther length: About 4 mm. Anther color: Close to 17A. Pollen amount: Moderate. Pollen color: Close to 17A. Gynoecium: Present on disc florets only. Pistil quantity per floret: One. Pistil length: About 1 cm. Style length: About 5 mm. Style color: Close to 144D. Stigma diameter: Less than 1 mm. Stigma shape: Bifurcate. Stigma color: Close to 17B. Ovary color: Close to 145C. Seeds: To date, seed development has not been observed on plants of the new *Dahlia*.

Pathogen & pest resistance: To date, plants of the new *Dahlia* have not been observed to be resistant to pathogens and pests common to *Dahlia* plants.

Temperature tolerance & garden performance: Plants of the new *Dahlia* tolerate high temperatures about 35° C. and low temperatures about 10° C. Plants of the new *Dahlia* have been observed to have good garden performance and to resist fading of the ray floret color under high light and high temperature conditions.

It is claimed:

1. A new and distinct *Dahlia* plant named 'Dodahyptrobre' as herein illustrated and described.

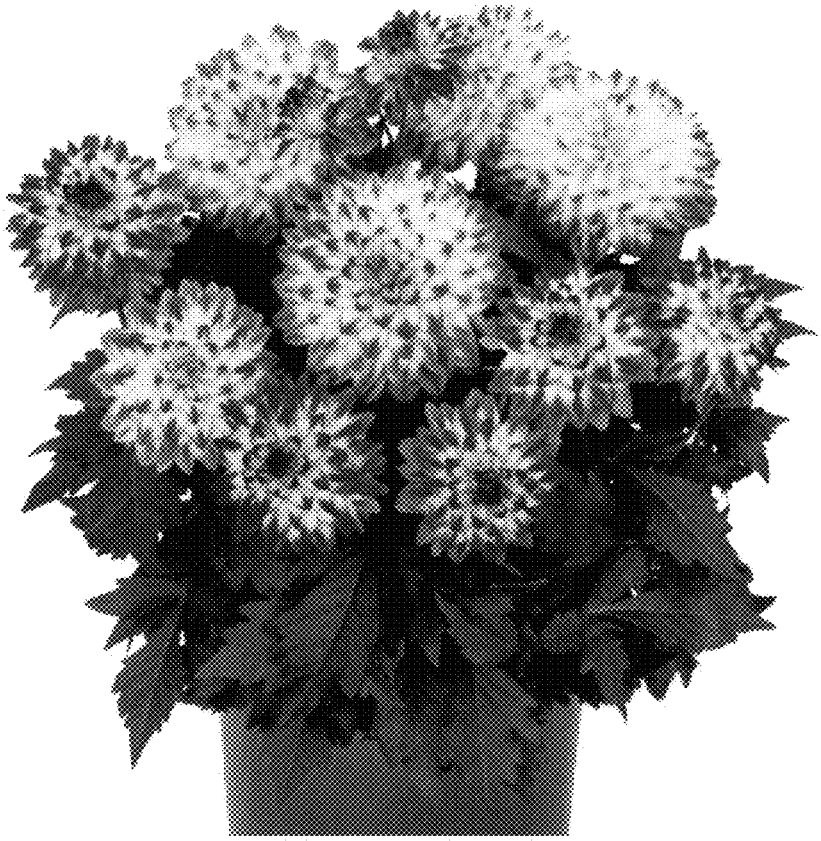

* * * * *